United States Patent [19]

Field et al.

[11] Patent Number: 4,460,781

[45] Date of Patent: Jul. 17, 1984

[54] 4-(2-BENZOYLPHENYL-1-PYAZOLE AND 4-(2-BENZOYLPHENYL)-1-PYRAZOLINE DERIVATIVES

[75] Inventors: George F. Field, West Caldwell; Rodney I. Fryer, North Caldwell; Eugene J. Trybulski, Parsippany; Armin Walser, West Caldwell, all of N.J.

[73] Assignee: Hoffmann-La Roche Inc., Nutley, N.J.

[21] Appl. No.: 455,767

[22] Filed: Jan. 5, 1983

Related U.S. Application Data

[60] Division of Ser. No. 286,122, Jul. 23, 1981, Pat. No. 4,379,765, which is a continuation-in-part of Ser. No. 175,552, Aug. 5, 1980, abandoned.

[51] Int. Cl.³ .................. C07D 231/06; C07D 231/14
[52] U.S. Cl. .................................. 548/356; 260/345.6; 424/273 P; 548/378
[58] Field of Search ............................... 548/356, 378

[56] References Cited

U.S. PATENT DOCUMENTS 4,028,381 6/1977 Gschwend ...................... 260/310 R Primary Examiner—Henry R. Jiles
Assistant Examiner—Kurt G. Briscoe
Attorney, Agent, or Firm—Jon S. Saxe; Bernard S. Leon; Frank P. Hoffman

[57] ABSTRACT

There are presented compounds of the formula

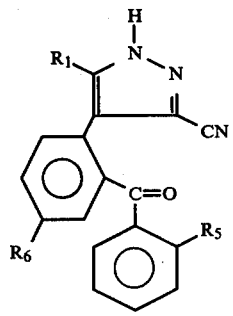

-continued

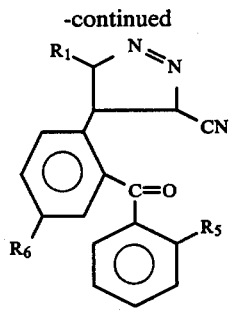

wherein $R_1$ is hydrogen or lower alkyl; $R_6$ is halo and $R_5$ is hydrogen or halo; and compounds of the formulas

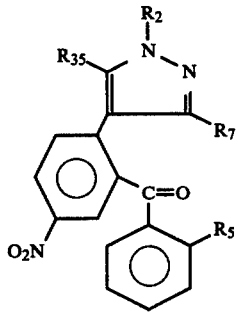

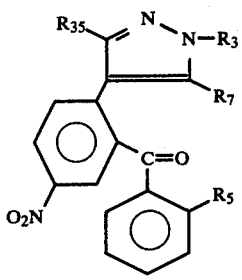

wherein $R_2$ and $R_3$ are selected from the group consisting of hydrogen, lower alkyl, $C_2$ to $C_7$ carboxylic acids, hydroxy $C_2$ to $C_7$ alkyl, $C_2$ to $C_7$ carboxylic acid esters and amides and the group $COR_{11}$ wherein $R_{11}$ and is selected from the group consisting of alkoxy, amino or mono-lower alkyl amino; $R_{35}$ is hydrogen or lower alkyl; $R_5$ is hydrogen or halo; and $R_7$ is methyl or chloromethyl, all of which are useful in the preparation of pyrazolobenzazepines.

8 Claims, No Drawings

4-(2-BENZOYLPHENYL-1-PYAZOLE AND 4-(2-BENZOYLPHENYL)-1-PYRAZOLINE DERIVATIVES

This is a division of application Ser. No. 286,122 filed July 23, 1981, now U.S. Pat. No. 4,379,765, which is a CIP of U.S. Ser. No. 175,552, filed Aug. 5, 1980 (now abandoned).

DESCRIPTION OF INVENTION

The present invention relates to pyrazolobenzazepines of the formulas

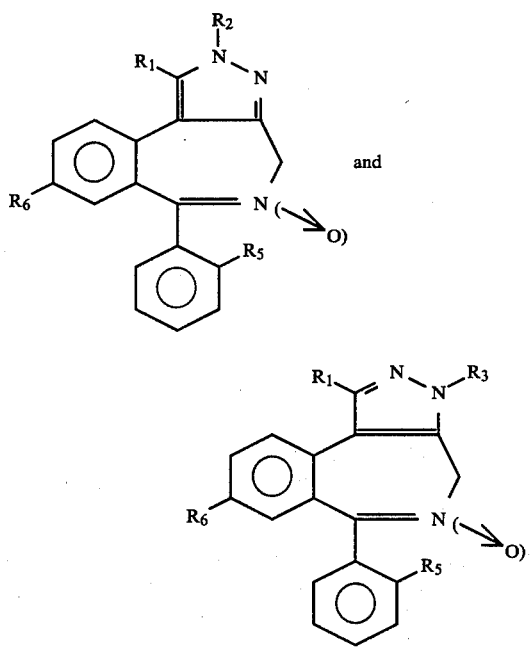

wherein $R_1$ is hydrogen or lower alkyl; $R_2$ and $R_3$ are selected from the group consisting of hydrogen, lower alkyl, $C_2$ to $C_7$ carboxylic acids, hydroxy $C_2$ to $C_7$ alkyl, $C_2$ to $C_7$ carboxylic acid esters and amides and the group $COR_{11}$ wherein $R_{11}$ is alkoxy, amino or mono- lower alkyl amino; $R_6$ is nitro or halo and $R_5$ is hydrogen or halo and the pharmaceutically acceptable salts thereof.

As used herein, the term "halo" or "halogen" or "halide" refers to chloro, bromo and fluoro unless otherwise indicated.

As used herein, the term "lower alkyl" refers to $C_1$ to $C_7$ carbon-hydrogen radicals which may be straight or branched chain, e.g. methyl, ethyl, propyl, isopropyl, butyl, etc.

By the term "$C_2$ to $C_7$ carboxylic acid esters and amides thereof" is meant substituents of the formulas lower alkyl —$COR_{15}$ wherein $R_{15}$ is hydroxy, alkoxy, amino or substituted amino. By substituted amino is meant an —$NH_2$ group which may be mono- or di-substituted by lower alkyl, e.g., methylamino or dimethylamino groups.

The N-oxides of compounds of formulas I and II may be formed by reaction of the base compounds with a peracid or by reaction in the case of a formula XVIII compound with hydroxylamine following reaction parameters well-known in the art.

The following reaction schemes set forth methods for the preparation of the compounds of formulas I and II.

Scheme I

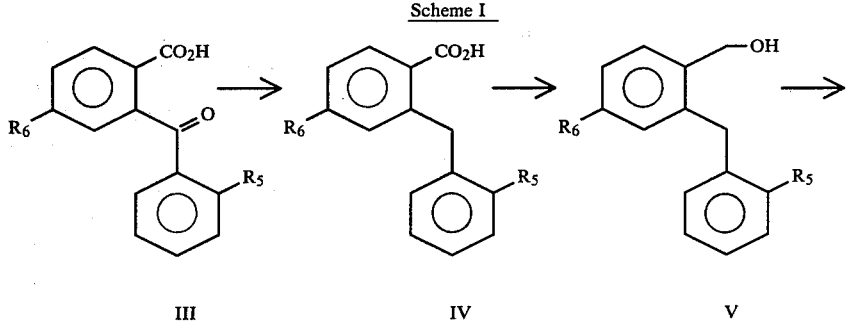

III  IV  V

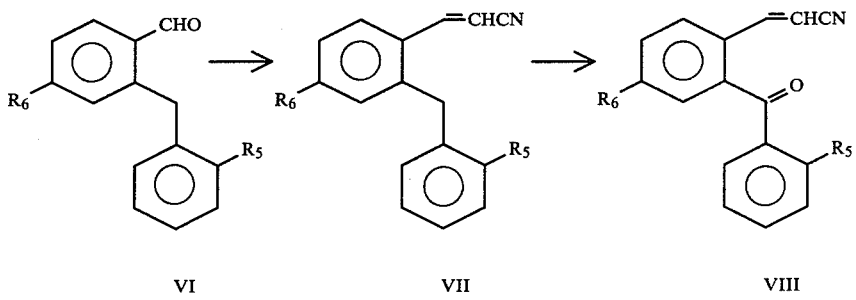

VI  VII  VIII

Scheme I

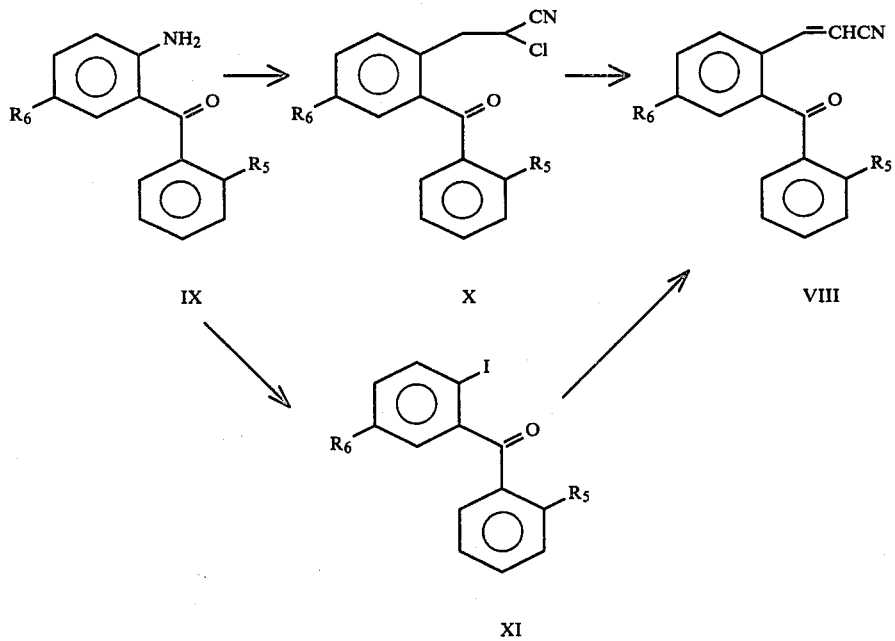

wherein R₅ is as above and R₆ is halo.

III→IV

The compound of formula III, a well-known starting material, is reacted with zinc dust and cupric sulfate in concentrated ammonium hydroxide. Reaction temperatures range from about room temperature to 100° C. with about 100° C. preferred.

IV→V

The compound of formula IV is reacted with a metal hydride, such as, lithium aluminum hydride or borane in an etherial solvent such as diethyl ether or tetrahydrofuran. Reaction temperatures range from about −78° C. to room temperature with about 0° C. preferred.

V→VI

The compound of formula V is reacted with pyridinium chlorochromate, manganese dioxide or other suitable oxidizing agents using methylene chloride as solvent. Reaction temperatures range from about 0° C. to the reflux temperature of the solvent with about room temperature as preferred.

VI→VII

The compound of formula VI is reacted with diethyl cyanomethylphosphonate in the presence of a strong base such as sodium hydride, sodium amide etc. and using an ethereal solvent, such as, tetrahydrofuran. Reaction temperatures range from about 0° C. to room temperature with about room temperature as preferred.

VII→VIII

The compound of formula VII is reacted with chromium trioxide or an oxidizing agent derived from chromium trioxide in a mixture of acetic acid and methylene chloride. Reaction temperatures range from about 0° C. to about 60° C. with room temperature preferred.

IX→X

The compound of formula IX i.e., the amino ketone is a well-known starting material. The compound is reacted with acrylonitrile in the presence of acetonitrile, a lower alkyl nitrite and cupric chloride. The reaction temperature may range from about 0° C. to about 40° C. with about room temperature as preferred.

X→VIII

The compound of formula X above is reacted with an alkali metal, e.g., lithium, sodium or potassium carbonate and bicarbonate mixture preferably a mixture of one part potassium carbonate to three parts potassium bicarbonate. Suitable solvents include DMSO, DMF or $C_1$ to $C_4$ alcohols, e.g., methanol. Reaction temperature ranges from about 20° C. to about 50° C. with room temperature preferred. The above reaction represents a dehydrohalogenation which is well-known in the art.

IX→XI

The compound of formula IX may be diazotized using sodium nitrite in sulfuric acid and the diazonium salt may be isolated by precipitating the respective tetrafluoroborate salts. These salts are slurried in water and treated with aqueous potassium iodide at room temperature to give the iodobenzophenone XI.

XI→VIII

The compound of formula XI is reacted with acrylonitrile in the presence of palladium II salt, such as, acetate using acetonitrile or an aromatic hydrocarbon, such as, toluene as solvent. Reaction temperatures range from about 60° C. to the reflux temperature of the solvent with reflux temperature preferred.

Scheme II

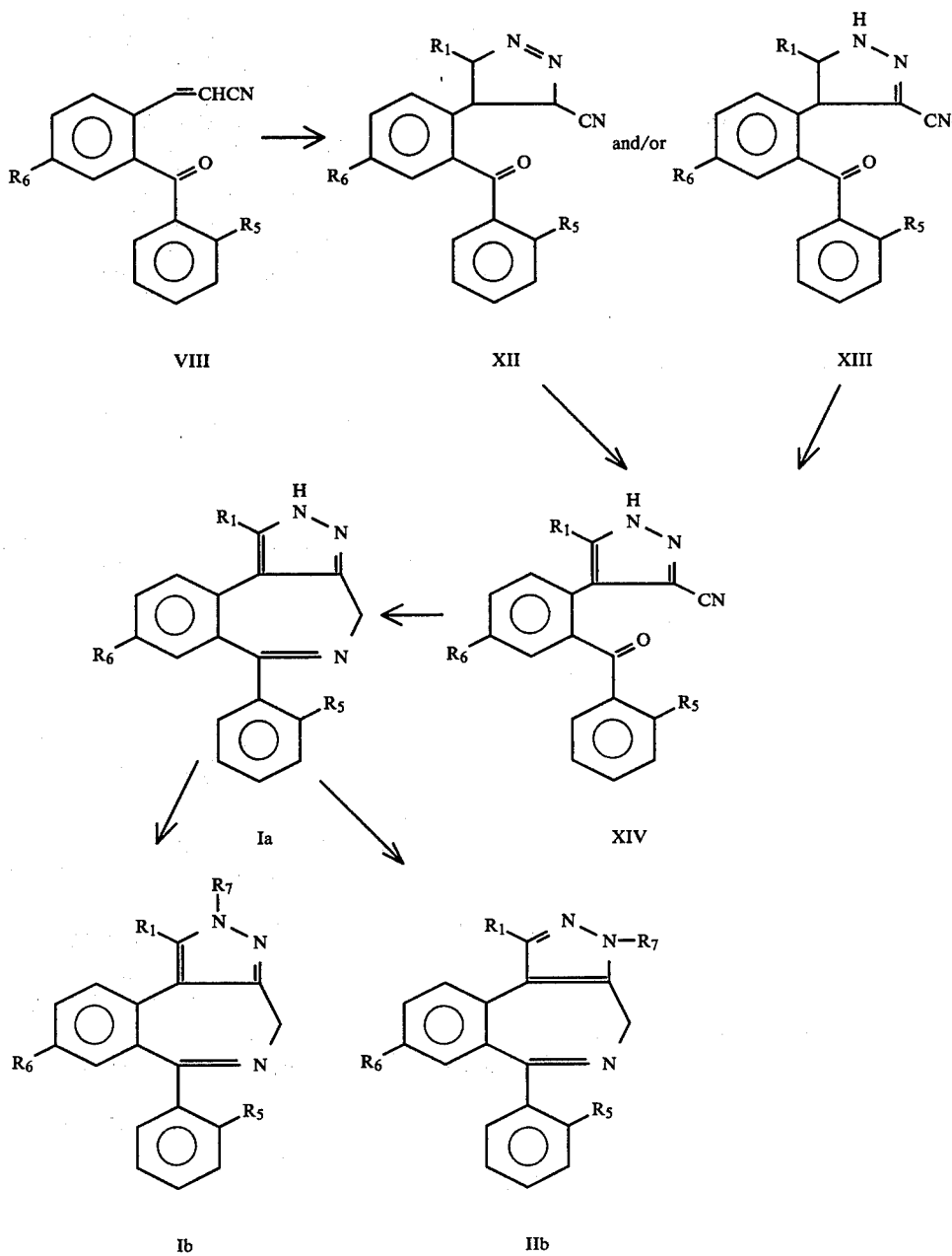

wherein $R_1$ and $R_5$ are as above and $R_6$ is halogen and $R_7$ is selected from the group consisting of lower alkyl or a $C_2$ to $C_7$ carboxylic acid ester.

VIII→XII and/or XIII

The compound of formula VIII is reacted with a diazoalkane of the formula $R_1$—$CHN_2$ wherein $R_1$ is as above.

Suitable solvents include ethereal solvents, such as, tetrahydrofuran or dioxane while utilizing methylene chloride as a co-solvent. The reaction is run at between about 0° C. to room temperature with about room temperature as preferred.

XII and/or XIII→XIV

The compounds of formulas XII and/or XIII are thereafter reacted with a dehydrogenating agent, such as, manganese dioxide in a compatible solvent, such as, toluene, tetrahydrofuran or methylene chloride. The reaction temperature may be varied from room temperature to the reflux temperature of the selected solvent with the reflux temperature preferred.

Alternatively compounds of formulas XII and/or XIII are reacted with bromine in a halogenated hydrocarbon solvent, such as, methylene chloride or chloroform at near room temperature. The dehydrogenation is effected by heating or by treatment with a mild base. The reaction mixture is then either heated to the reflux temperature of the solvent or treated with a mild base, such as, an alkali metal bicarbonate or trialkylamine.

XIV→Ia

The compound of formula XIV is reacted with hydrogen at pressures ranging from about atmospheric pressure to five atmospheres in the presence of a transition metal catalyst, such as, Raney nickel using glacial acetic acid as solvent. Reaction temperature is about room temperature. The open amine is first formed in the reduction of XIV and then cyclizes to Ia.

Ia→Ib and IIb

The compound of formula Ia is reacted with an alkali metal alkoxide, such as, sodium or potassium methoxide or ethoxide, or a lithium di-lower alkyl amide followed by a secondary reaction with an alkylating agent, such as, a lower alkyl halide or sulfonate in an ethereal solvent, such as, tetrahydrofuran, dioxane, dimethylformamide or dimethylsulfoxide. The secondary reaction may also be effected by reaction with a haloester, such as, an ethylbromoacetate or ethyl-3-bromopropionate to produce a compound wherein $R_7$ is a $C_2$ to $C_7$ carboxylic acid ester. The reaction may be run at between about 0° C. to room temperature with about 0° C. as preferred.

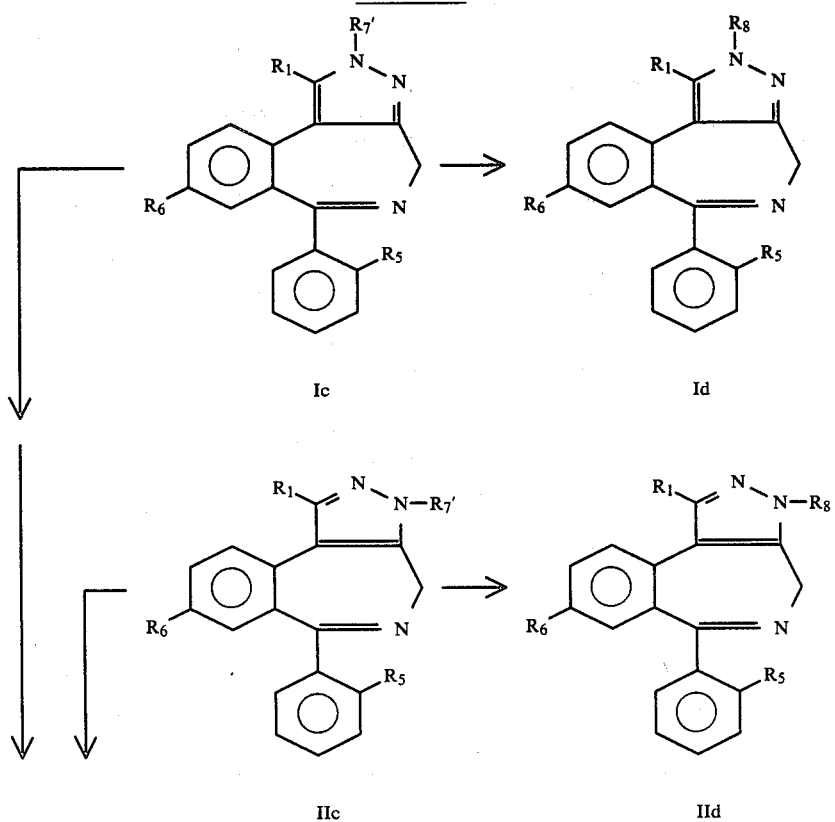

Scheme III

-continued

Scheme III

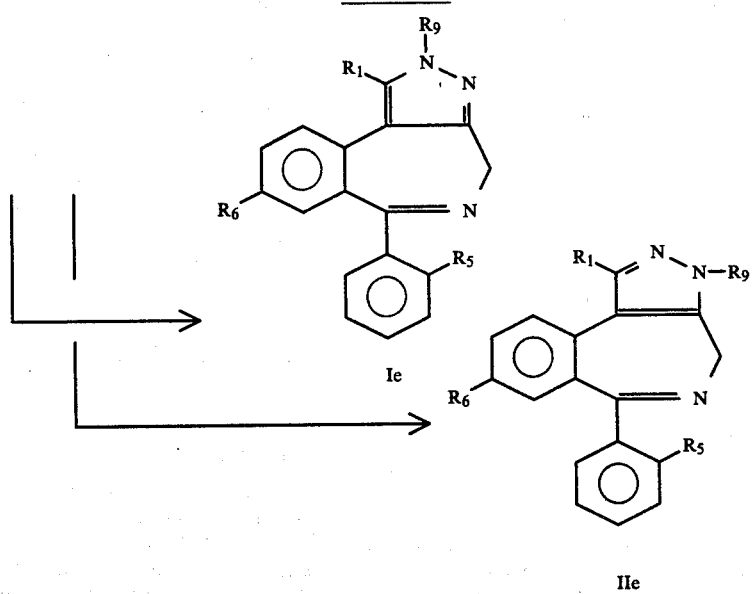

wherein $R_1$ and $R_5$ are as above and $R_6$ is halogen, $R_7'$ is a $C_2$ to $C_7$ carboxylic acid ester, $R_8$ is a carboxylic acid amide and $R_9$ is hydroxy $C_2$ to $C_7$ alkyl.

Ic→Id and IIc→IId

The compounds of formulas Ic and IIc are reacted with ammonia or a mono- or di-substituted lower alkyl amine and a catalytic amount of the complementary hydrochloride salt in a $C_1$ to $C_4$ alcoholic solvent. The reaction is run at about 100° C. utilizing a pressure apparatus to contain the volatile reactants.

Ic→Ie and IIc→IIe

The compounds of formulas Ic and IIc are reacted with a metal hydride reducing agent, such as, lithium aluminum hydride in an ethereal solvent, such as, tetrohydrofuran or dioxane.

The reaction is run at about −78° C. to room temperature with about 0° C. as preferred.

Scheme IV

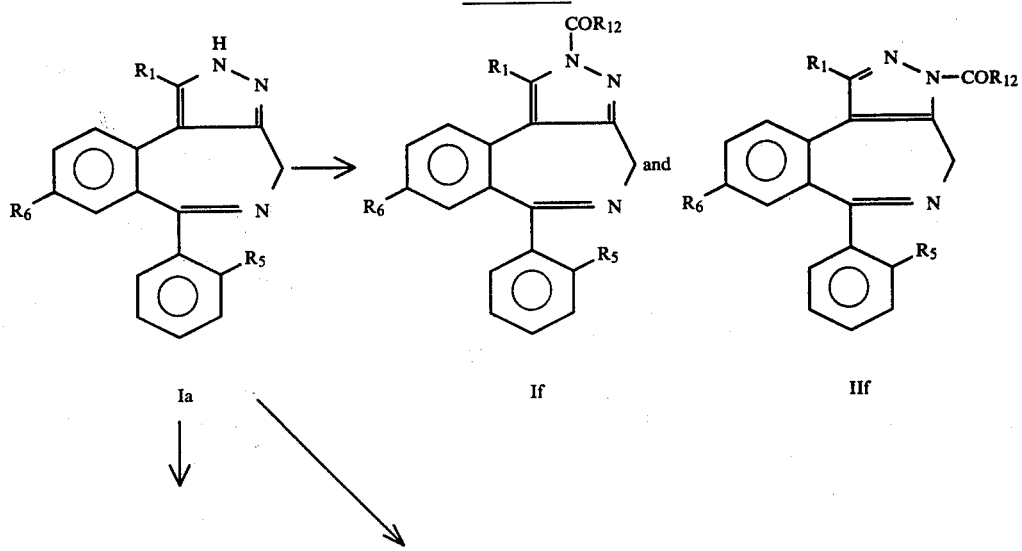

-continued
Scheme IV

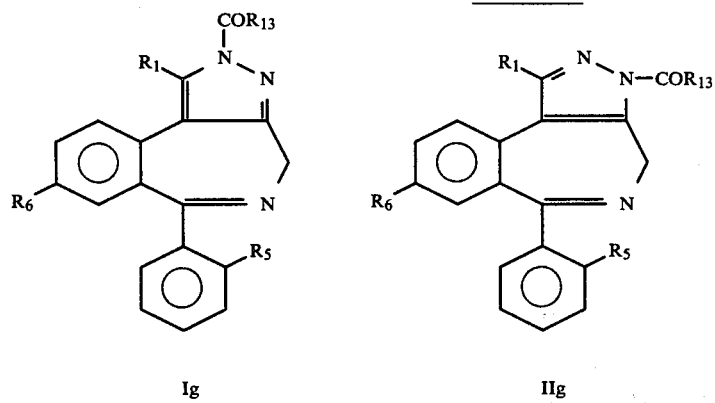

wherein $R_1$ and $R_5$ are as above and $R_6$ is halogen, $R_{12}$ is amino or mono- lower alkylamino and $R_{13}$ is lower alkoxy

Ia→If and IIf

The compound of formula Ia is reacted with a lower alkyl or alkali metal isocyanate in an ethereal solvent, such as, tetrahydrofuran or dixane of a chlorinated hydrocarbon, such as, methylene chloride or chloroform. The reaction is effected at from about −20° C. to room temperature with about 0° C. as preferred.

Ia→Ig and IIg

The compound of formula Ia is reacted with an alkali metal alkoxide, such as, a sodium or potassium ethoxide or butoxide or with a lithium di-lower alkylamide followed by a halo formate, such as, methyl chloroformate, benzyl chloroformate, etc. in an ethereal solvent, such as, tetrahydrofuran or dioxane or in dimethylformamide. The reaction is run at between about −78° C. to room temperature with about 0° C. as preferred.

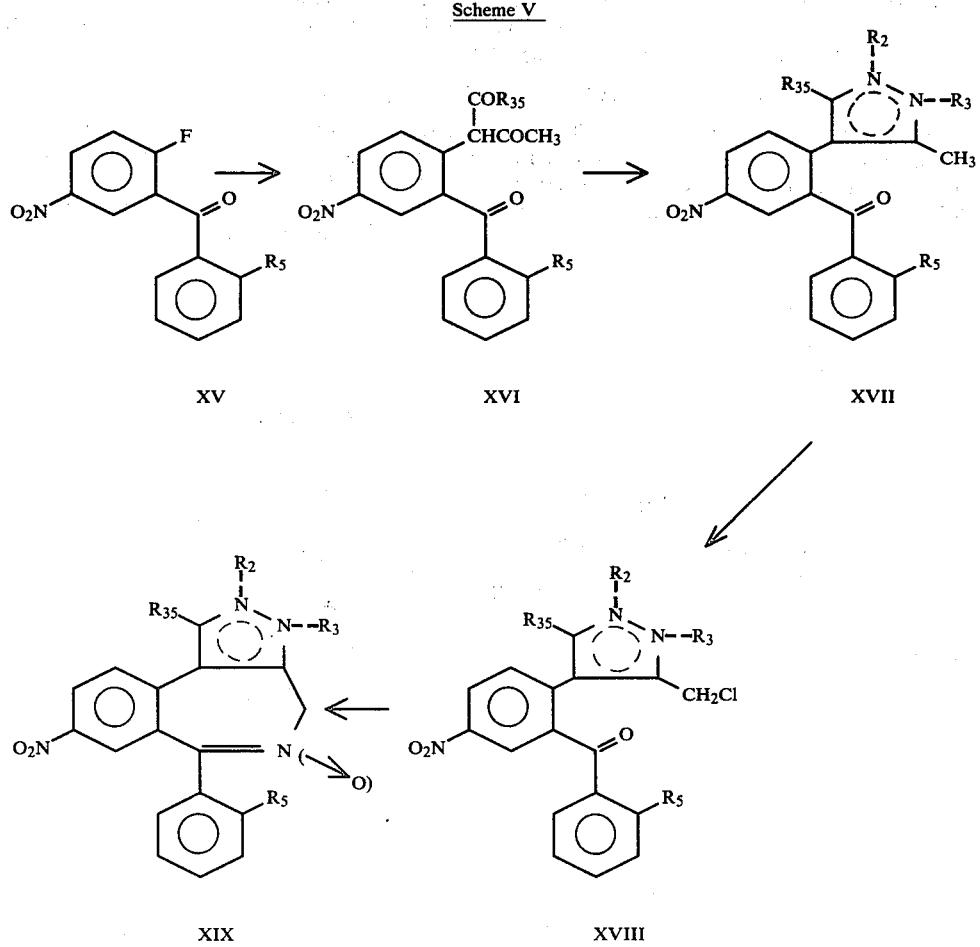

Scheme V wherein $R_2$, $R_3$ and $R_5$ are as above, $R_{35}$ is hydrogen or lower alkyl.

The dotted lines found at the $R_2$ and $R_3$ substitution points and in the pyrazolo-ring indicate the alternate nature of substitution and unsaturation, i.e., where there is a $R_2$ then there is no $R_3$ and the unsaturation occurs at 1,2 and 4,5 whereas when there is a $R_3$ substituent, then unsaturation is 2,3 and 1,5.

Following the reactions of steps Ia→Ib, Ia→IIb, Ic→Id, IIc→IId the compound of formula XIX wherein $R_2$ and $R_3$ are hydrogen may be modified to provide $R_2$ and $R_3$ equal to lower alkyl, $C_2$ to $C_7$ carboxylic acid esters and amides and the group $COR_{11}$ wherein $R_{11}$ is alkoxy, amino or mono-lower alkylamino.

XV→XVI

The compound of formula XV may be produced by following methods known in the art.

The compound of formula XV is reacted with a dicarbonyl compound of the formula

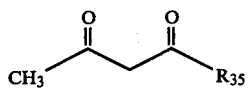

wherein $R_{35}$ is as above
in the presence of a strong base, such as sodium hydride or a potassium or sodium methoxide. Suitable solvents are polar aprotic solvents, such as, dimethylsulfoxide, dimethylformamide or tetrahydrofuran. The reaction may be run from between about $-10°$ C. to $100°$ C. with about room temperature preferred.

XVI→XVII

The compound of formula XVI is thereafter reacted with a hydrazine salt or a substituted hydrazine salt, a hydrazine substituted with the particular $R_2$ or $R_3$ substituent which is desired. The salts may be mineral acid salts, such as, the hydrochlorides or sulfates. Suitable solvents include $C_1$ to $C_4$ aqueous alcoholic solutions. The reaction may be run at from about room temperature to reflux temperature with reflux temperature of the selected solvent as preferred.

XVII→XVIII

The compound of formula XVII is thereafter reacted with a halogenating agent, such as, t-butyl hypochlorite or N-bromosuccinimide. Suitable solvents include non-polar solvents, such as, methylene chloride, benzene or toluene. The reaction may be run at between about $0°$ C. to reflux temperature of the solvent with about room temperature as preferred.

XVIII→XIX

The compound of formula XVIII is reacted with ammonia or hydroxylamine in the presence of a solvent, such as, tetrahydrofuran, dimethylformamide, dimethylsulfoxide and methylene chloride. The reaction is carried out at between about $-40°$ C. to reflux with a preferred range of from about room temperature to $50°$ C. The open hydroxylamine spontaneously cyclizes to the desired end product.

Preferred compounds of formulas I and II are those wherein $R_1$ is as above, $R_2$ and $R_3$ are hydrogen and lower alkyl and $R_5$ and $R_6$ are as above.

Especially preferred compounds of formulas I and II are those of the formulas:

8-chloro-6-(2-fluorophenyl)-2H,4H-pyrazolo[3,4-d][2]benzazepine 8-chloro-6-phenyl-2-(2-hydroxyethyl)-2H,4H-pyrazolo[3,4-d][2]benzazepine 6-(2-chlorophenyl)-3-methyl-8-nitro-2H,4H-pyrazolo[3,4-d][2]benzazepine 8-chloro-2-/(methylamino)carbonyl/-6-phenyl-2H,4H-pyrazolo[3,4-d][2]benzazepine The expression "pharmaceutically acceptable salts" is used to include salts with both inorganic and organic pharmaceutically acceptable strong acids, such as, sulfuric acid, hydrochloric acid, nitric acid, methanesulfonic acid and p-toluenesulfonic acid. Such salts can be formed quite readily by those skilled in the art with the prior art and the nature of the compound to be placed in salt form in view.

The pharmaceutical activities of the instantly claimed compounds are indicated by the pharmacological data set forth below for the compounds of the invention.

| Compounds | Tests Footshock | Inclined Screen | Unanesthetized Cat |
|---|---|---|---|
| 8-chloro-2-(methyl-amino)carbonyl-6-phenyl-4H—pyrazolo-3,4-d-2-benzazepine | 25 mg/kg | 400 mg/kg | 20 mg/kg |
| 8-(2-chlorophenyl)-3-methyl-6-nitro-2H,10H—pyrazolo-3,4-d-2-benzazepine Toxicity (LD$_{50}$) = greater than 1000 mg/kg (PO) | | 400 mg/kg | 250 mg/kg |
| 8-chloro-6-(2-chloro-phenyl)-2H,4H—pyrazolo-3,4-d-2-benzazepine half molar dichloromethane solvate Toxicity (LD$_{50}$) = 800 mg/kg (PO) | 25 mg/kg | 143 mg/kg | 10 mg/kg |
| 8-chloro-2-(2-hydroxy-ethyl)-6-phenyl-2H,4H—pyrazolo-3,4-d-2-benzazepine Toxicity (LD$_{50}$) = 750 mg/kg (PO) | 100 mg/kg | 40 mg/kg | 20 mg/kg |
| 8-chloro-6-(2-fluoro-2H,4H-pyrazolo-3,4-d-2-benzazepine Toxicity (LD$_{50}$) = 760 mg/kg (PO) | 25 mg/kg | 66 mg/kg | 2 mg/kg |

A summary of the pharmacological tests which are known in the art is as follows.

Footshock

A pair of mice is confined under a one liter beaker placed on a grid which presents shock to the feet. At least 5 fighting episodes are elicited in a two-minute period. Pairs of mice are marked and pretreated 1 hour to a second shocking. Logarithmic dose intervals are utilized up to a maximum of 100 mg/kg. At the 100% blocking dose, 3 out of 3 pairs must be blocked from fighting.

Inclined Screen

Groups of 6 male mice are given the test drug (maximum dose of 500 mg/kg) and then are left on the inclined screen at least 4 hours for observation of paralyzing effects severe enough to cause them to slide off the screen. If activity is observed, additional doses are taken until at least two are reached at which some, but not all of the animals slide off the screen. Doses at which mice fall off the screen due to toxicity or excitation are not included in the calculation of $PD_{50}$.

Unanesthetized Cat

Cats are treated orally and observed for minimum symptoms—usually ataxia. One cat is used at a dose of 50 mg/kg. If activity is present, up to three cats/dose are used. Results are given as minimum effective dose.

The pyrazolo[3,4-d][2]benzazepines above are useful as pharmaceuticals and are characterized by activity as sedatives and anxiolytic agents. These compounds can be used in the form of conventional pharmaceutical preparations; for example, the aforesaid compounds can be mixed with conventional organic or inorganic, inert pharmaceutical carriers suitable for parenteral or enteral administration such as for example, water gelatin, lactose, starch, magnesium stearate, talc, vegetable oil, gums, polyalkylene glycols, Vaseline or the like. They can be administered in conventional pharmaceutical forms, e.g., solid forms, for example, tablets, dragees, capsules, suppositories or the like, or in liquid forms, for example, solutions, suspensions or emulsions. Moreover, the pharmaceutical compositions containing compounds of this invention can be subjected to conventional pharmaceutical expedients such as sterilization, and can contain conventional pharmaceutical excipients such as preservatives, stabilizing agents, wetting agents, emulsifying agents, salts for the adjustment of osmotic pressure, or buffers. The compositions can also contain other therapeutically active materials.

A suitable pharmaceutical dosage unit can contain from about 1 to about 500 mg of the benzazepine end products with a dosage range of from about 1 mg to about 100 mg being the preferred oral administration and a dosage range of from about 1 mg to about 50 mg being preferred for parenteral administration. However, for any particular subject, the specific dosage regiment should be adjusted according to individual need and the professional judgement of the person administering or supervising the administration of the aforesaid compounds. It is to be understood that the dosages set forth herein are exemplary only and that they do not, to any extent, limit the scope or practice of this invention.

The term "dosage unit" as employed throughout this specification refers to pharmaceutically discrete units suitable as unitary dosages for mammalian subject each containing a predetermined quantity of active material calculated to produce the desired therapeutic effect in association with the required pharmaceutical diluent, carrier or vehicle.

The following examples are illustrative, but not limitative of this invention. All temperatures given are in degrees centigrade, unless indicated otherwise.

EXAMPLE 1

2-Benzyl-4-chlorobenzoic Acid

To a solution of 5.0 g of cupric sulfate in 3 liters of concentrated ammonium hydroxide was added 300 g (4.6 mole) of activated zinc dust and 100 g (0.42 mole) of 2-benzoyl-4-chlorobenzoic acid. The mixture was refluxed for 3 days, during which the volume was maintained by the addition of concentrated ammonium hydroxide. The mixture was cooled, and the excess zinc was removed by filtration. The filtrate was acidified by the addition of concentrated hydrochloric acid to a pH of 3. The resulting precipitate was collected by filtration, and dried to constant weight to give a white solid with mp 142°–144°.

EXAMPLE 2

2-Benzyl-4-chlorobenzyl alcohol

To a solution of 28.4 g (0.75 mole) of lithium aluminum hydride in 800 ml of ether, which was cooled to 0°, was added dropwise 85.1 g (0.345 mmole) of 2-benzyl-4-chlorobenzoic acid in 250 ml of ether. The mixture was allowed to warm to room temperature, and was stirred for 2 hr. The excess lithium aluminum hydride was discharged by the addition of 28.5 ml of water, 28.5 ml of 10% aqueous sodium hydroxide, and 85.5 ml of water. The precipitate was removed by filtration and the filtrate was dried with sodium sulfate. Removal of the ether at reduced pressure gave a colorless oil which crystallized upon standing, mp 46.5°–49°.

EXAMPLE 3

2-Benzyl-4-chlorobenzaldehyde

To a suspension of 238 g (1.1 mole) of pyridinium chlorochromate and 800 ml of methylene chloride was added 79.3 g (0.34-mole) of 2-benzyl-4-chlorobenzyl alcohol. The mixture was stirred at room temperature for 2 hr. The chromium salts were precipitated by the addition of 2.4 liters of 1:1 ether:petroleum ether, and the precipitate was removed by filtration through Celite. The solvent was removed at reduced pressure to give a yellow oil, which was used without further purification.

EXAMPLE 4

3-[2-Benzyl-4-chlorophenyl]-2-propenonitrile

To a suspension of 10.5 g (0.437 mole) of mineral oil free sodium hydride in 1.2 liters of tetrahydrofuran was added dropwise 58.4 g (0.328 mole) of diethylcyanomethyl phosphonate. After the hyrogen evolution had ceased ca 60 min, 69.4 g (0.3 mole) of 2-benzyl-4-chlorobenzaldehyde, in 75 ml of tetrahydrofuran was added dropwise. The mixture was stirred overnight at room temperature. The tetrahydrofuran solution was decanted, and concentrated at room temperature. The residue was partitioned between 2 liters of water and 1.5 liters of ether. The ether solution was separated, washed with water, and dried with sodium sulfate. The ether was removed at reduced pressure to give a yellow oil which was used without further purification.

EXAMPLE 5

4-[2-Benzoyl-4-chlorophenyl]pyrazole-3-carbonitrile

A mixture of 0.4 mole of diazomethane in 400 ml of ether and 18.2 g (0.068 mole) of 3-(2-benzoyl-4-chlorophenyl)-2-propenonitrile was allowed to stand at room temperature overnight. The excess diazomethane was discharged by the dropwise addition of 30 ml of acetic acid. The ether solution was washed with 5% aqueous sodium carbonate and water. The ether solution was dried ($Na_2SO_4$), and was concentrated at reduced pressure to give a yellow oil.

A mixture of 21.0 g of the yellow oil, 11.1 g (0.069 mole) of bromine, 17 g (0.204 mole) of sodium bicarbonate and 300 ml of chloroform was stirred at room temperature overnight. The excess bromine was discharged by the addition of 200 ml of saturated aqueous sodium bisulfite. The chloroform solution was separated, washed with water, and dried with sodium sulfate. Concentration of the chloroform solution at reduced pressure gave a yellow oil. Purification by column chromatography (800 g, $SiO_2$; 4:1 methylene chloride:ether) gave a white solid, mp 194°–195°.

EXAMPLE 6

8-Chloro-6-phenyl-2H,4H-pyrazolo[3,4-d][2]-benzazepine

A mixture of 2.2 g (7.2 mmole) of 4-[2-benzoyl-4-chlorophenyl]pyrazole-3-carbonitrile, 2.0 g of Raney nickel, and 150 ml of acetic acid was hydrogenated on a Parr apparatus for 4 hr. The Raney nickel was removed by filtration, and the filtrate diluted with 600 ml of ice water. The acetic acid was neutralized with concentrated ammonium hydroxide and the resulting aqueous solution was extracted with methylene chloride. The methylene chloride solution was washed with water, and was dried with sodium sulfate. Concentration of the methylene chloride solution gave a tan solid. Recrystallization from chloroform/hexane gave a white solid, mp 241°–243°.

EXAMPLE 7

4-(2-benzoyl-4-chlorophenyl)-3-cyano-5-methyl-pyrazole

A solution of diazoethane in 400 ml of ether (prepared from 16.1 g (0.1 mol) of N-ethyl-N'-nitro-N-nitrosoimino urea,) was added to a solution of 15 g (0.056 mol) of crude 3-(2-benzoyl-4-chlorophenyl)-2-propenonitrile in 100 ml of ether. After standing at room temperature for 3 hr, the excess diazoethane was destroyed by addition of glacial acetic acid. The mixture was washed with saturated sodium bicarbonate solution, was dried and evaporated, at the end azeotropically with toluene. The residue was dissolved in 400 ml of toluene and the solution was heated to reflux for 1½ hr in presence of 60 g of activated manganese dioxide. The water was separated in a Dean Stark trap. The $MnO_2$ was removed by filtration over Celite and the filtrate was evaporated. The residue (14 g) was chromatographed over 300 g of silica gel using 10% (v/v) of ethyl acetate in methylene chloride. The homogenous fractions were combined and evaporated to yield an oily product.

EXAMPLE 8

8-Chloro-1-methyl-6-phenyl-2H,4H-pyrazolo[3,4-d][2]benzazepine

A mixture of 1.8 g of resinous 4-(2-benzoyl-4-chlorophenyl)-3-cyano-5-methylpyrazole, 35 ml of glacial acetic acid and ca. 10 g of Raney nickel was hydrogenated at atmospheric pressure for 6 hr. The catalyst was filtered off and the filtrate was evaporated. The residue was partitioned between methylene chloride/ether and 10% aqueous sodium carbonate solution. The organic phase was dried and evaporated and the residue was crystallized from ether to yield crude product which was recrystallized from ether to give off-white crystals with mp 145°–150° (foaming).

The mother liquor was chromatographed over 30 g of silica gel using ethyl acetate/methylene chloride 3:1. Crystallization of the combined clean fractions from ether/hexane gave additional product.

This was combined with the first crop and dissolved in hot ethanol. Ethanolic hydrogen chloride was added and the hydrochloride was crystallized by addition of ether. The yellow needles were collected and dried to yield end product with mp 290°–295°. The analytical sample was recrystallized from methanol/ether.

EXAMPLE 9

8-Chloro-N-methyl-6-phenyl-2H,4H-pyrazolo[3,4-d][2]benzazepine-2-carboxamide and 8-Chloro-N-methyl-6-phenyl-3H,4H-pyrazolo[3,4-d][2]benzazepine-3-carboxamide Methyl isocyanate, 2 ml, was added to a solution of 0.9 g (3.07 mmol) of 8-chloro-6-phenyl-2H,4H-pyrazolo[3,4-d][2]benzazepine in 50 ml of methylene chloride and the mixture was allowed to stand at room temperature for 2 hr. The solvent was evaporated and the residue was crystallized from ethyl acetate to yield the 2-carboxamide as white needles with mp 230°–235°.

The mother liquor was evaporated and the residue was chromatographed over 65 g of silica gel using 20% (v/v) of ether in benzene. Crystallization of the combined clean fractions from ethyl acetate/hexane gave the 3-carboxamide with mp 188°–190° and 248°–250° dec.

EXAMPLE 10

8-Chloro-6-phenyl-2H,4H-pyrazolo[3,4-d][2]benzazepine-2-acetic acid ethyl ester and 8-Chloro-6-phenyl-3H,4H-pyrazolo[3,4-d][2]benzazepine-3-acetic acid ethyl ester To a solution of 1.2 g (4.1 mmole) of 8-chloro-6-phenyl-2H,4H-pyrazolo[3,4-d][2]benzazepine in 35 ml of dry tetrahydrofuran, which was cooled to −20°, was added 9.0 ml (4.5 mmole) of a 0.5M tetrahydrofuran solution of lithium disopropylamine. The mixture was allowed to warm to room temperature followed by the addition of 0.5 ml (4.5 mmole) of ethyl bromoacetate. The mixture was stirred for 5 hr at room temperature, was poured into 100 ml of water, and was extracted with ether. The ether solution was dried with sodium sulfate, and concentrated at reduced pressure to give a yellow foam. Purification by column chromatography (30 g $SiO_2$, 9:1 methylene chloride/ether) gave two major components: the 3-acetic acid ethyl ester as a yellow foam. The later fractions gave the 2-acetic acid ethyl ester as a yellow foam.

EXAMPLE 11

8-Chloro-6-phenyl-2H,4H-pyrazolo[3,4-d][2]benzazepine-2-acetamide

Heating a mixture of 0.8 g (2.1 mmol) of 8-chloro-6-phenyl-2H,4H-pyrazolo[3,4-d][2]benzazepine-2-acetic acid ethyl ester and 20 ml of methanolic ammonia (ca. 20%, v/v) in an autoclave on the steam bath for 20 hr gave after crystallization from ethyl acetate/ether colorless crystals with mp 236°–238°. The analytical sample was recrystallized from ethyl acetate/methylene chloride/ether.

EXAMPLE 12

8-Chloro-6-phenyl-3H,4H-pyrazolo[3,4-d][2]benzazepine-3-acetamide

A mixture of 0.4 g (1.05 mmol) of 8-chloro-6-phenyl-3H,4H-pyrazolo[3,4-d][2]benzazepine-3-acetic acid ethyl ester and 20 ml of methanolic ammonia (ca 20% v/v) was heated in an autoclave on the steam bath overnight. The solvent was evaporated and the residue was purified by chromatography over 15 g of silica gel using 5% (v/v) of ethanol in methylene chloride. Crystallization from ethyl acetate/ether gave colorless crystals with mp 218°–219°.

EXAMPLE 13

8-Chloro-2-(2-hydroxyethyl)-6-phenyl-2H,4H-pyrazolo[3,4-d][2]benzazepine

A solution of 0.4 g (0.01 mol) of lithium aluminum hydride in 80 ml of ether was cooled to −30°. A solution of 0.8 g (2.1 mmol) of 8-chloro-6-phenyl-2H,4H-pyrazolo[3,4-d][2]benzazepine-2-acetic acid ethyl ester in 5 ml of tetrahydrofuran was added and the mixture was stirred at −10° to −5° for 15 min. The reaction mixture was hydrolyzed by addition of 2 ml of water, diluted with methylene chloride and filtrated over Celite. The filtrate was evaporated and the residue was crystallized from ether to yield colorless crystals which were recrystallized for analysis from ethyl acetate, hexane, mp 173°–175°.

EXAMPLE 14

3-(2-Benzoyl-4-chlorophenyl)-2-propenenitrile

A mixture of 28.8 g (0.14 mole) of 3-[2-benzyl-4-chlorophenyl]-2-propenentrile, 50 g (0.5 mole) of chromium trioxide, 100 ml of methylene chloride, and 300 ml of acetic acid was stirred at room temperature overnight. The excess chromium trioxide was discharged by the slow addition of 30 ml of ethanol. The mixture was diluted with 800 ml of water, and extracted with 500 ml of ether. The ether solution was washed with water, saturated aqueous sodium bicarbonate, and saturated aqueous sodium chloride. The ether solution was dried with anhydros sodium sulfate, and concentrated at reduced pressure to give a yellow oil which was used without further purification.

A sample of the product was purified by preparative layer chromatography (SiO₂; 2 mm; 1:1 methylene chloride:pentane) to give a white solid, mp 87°–89°.

EXAMPLE 15

α,4-dichloro-2-(benzoyl)-benzenepropanenitrile

A solution of 92.7 g (0.4 mole) of 2-amino-5-chlorobenzophenone in 250 ml of acetonitrile was added to a mixture of 70 g (0.52 mole) of cupric chloride, 65 g (0.63 mole) of t-butylnitrite, 500 ml of acrylonitrile, and 500 ml of acetonitrile. When the addition was complete stirring at room temperature was continued for 2 hr. The mixture was diluted with 80 ml of 6N hydrochloric acid and 1500 ml of water, extracted with ether and dried over anhydrous sodium sulfate. The ether solution was concentrated at reduced pressure to give a brown oil, which contained the end product and 2,5-dichlorobenzophenone. Trituration of the oil with a mixture of ether and petroleum ether gave the end product as a tan solid. Recrystallization of a small portion of the end product from a mixture of ether and petroleum ether gave pale yellow needles, mp 69°–71°.

EXAMPLE 16

α,4-dichloro-2-(2-fluorobenzoyl)-benzenepropanenitrile

The preparation of α-4-dichloro-2-(2-fluorobenzoyl)-benzenepropanenitrile was conducted in the same manner as the preparation of α-4-dichloro-2-(benzoyl)-benzenepropanenitrile to give pale yellow prisms, mp 94°–95°.

EXAMPLE 17

α,4-dichloro-2-(2-chlorobenzoyl)-benzenepropanenitrile

The preparation of α,4-dichloro-2-(2-chlorobenzoyl)-benzenepropanenitrile was conducted in the same manner as the preparation of α,4-dichloro-2-(benzoyl)-benzenepropanenitrile to give off-white prisms, mp 102°–103°.

EXAMPLE 18

3-(2-benzoyl-4-chlorophenyl)-2-propanenitrile

A mixture of 50.9 g (0.168 mole) of α,4-dichloro-2-(benzoyl)-benzenepropanenitrile, 17 g (0.14 mole) of potassium carbonate, 50.9 g (0.5 mole) of potassium bicarbonate and 510 ml of dimethyl sulfoxide was stirred at room temperature for 48 hr. The mixture was diluted with 1.5 l of water, and the resulting percipitate was collected by filtration. Recrystallization from a mixture of methylene chloride and ether gave off-white prisms, mp 89°–91°.

EXAMPLE 19

3-[2-(2-fluorobenzoyl)-4-chlorophenyl]-2-propenenitrile

The preparation of 3-[2-(2-fluorobenzoyl)-4-chlorophenyl]-2-propenenitrile was conducted in the same manner as the preparation of 3-(2-benzoyl-4-chlorophenyl)-2-propenenitrile to give off-white prisms, mp 137°–139°.

EXAMPLE 20

3-[2-(2-Chlorobenzoyl)-4-chlorophenyl]-2-propenenitrile

The preparation of 3-[2-(2-chlorobenzoyl)-4-chlorophenyl]-2-propenenitrile was conducted in the same manner as the preparation of 3-(2-benzoyl-4-chlorophenyl)-2-propenenitrile to give off-white prisms, mp 140°–141°.

EXAMPLE 21

4-[2-(2-Fluorobenzoyl)-4-chlorophenyl]-1H-pyrazole-3-carbonitrile

A mixture of 7.0 g (24.5 mmole) of 3-[4-chloro-2-(2-fluorobenzoyl)phenyl)]-2-propenenitrile, 100 ml (100 mmole) of a 1M ether solution of diazomethane and 75 ml of methylene chloride was allowed to stand at room temperature for 6 hr. The excess diazomethane was discharged by the addition of acetic acid. The resulting solution was washed with 5% aqueous sodium bicarbonate, dried over anhydrous sodium sulfate and concentrated at reduced pressure to give an amber oil.

A mixture of 8.5 g of the amber oil, 2.0 ml (36.5 mmole) of bromine and 150 ml of chloroform was stirred at room temperature for 45 min. The volatiles were removed at reduced pressure and the residue was redissolved in 100 ml of chloroform. The chloroform solution was boiled on the steam bath for 30 min. The chloroform solution was washed with 5% aqueous sodium bicarbonate, dried over anhydrous sodium sulfate and concentrated at reduced pressure to give an amber oil. Purification by column chromatography (SiO$_2$, 100 g; eluent 5% ether in methylene chloride) gave as the major component the end product as pale yellow prisms, mp 169°–170°.

EXAMPLE 22

4-[2-(2-Chlorobenzoyl)-4-chlorophenyl)-1H-pyrazole-3-carbonitrile

The preparation of 4-[2-(2-chlorobenzoyl)-4-chlorophenyl]-1H-pyrazolo-3-carbonitrile was conducted in the same manner as the preparation of 4-[2-(2-fluorobenzoyl)-4-chlorophenyl]-1H-pyrazole-3-carbonitrile to give pale yellow prisms, mp 183°–184°.

EXAMPLE 23

8-Chloro-6-(2-fluorophenyl)-2H,4H-pyrazolo[3,4-d][2]benzazepine

A mixture of 2.0 g (6.1 mmole) of 4-[2-(2-fluorobenzoyl)-4-chlorophenyl]-1H-pyrazole-3-carbonitrile, ca 2 g. of Raney nickel, and 100 ml of acetic acid was hydrogenated on a Parr apparatus for 4 hr. The Raney nickel was removed by filtration and the acetic acid was removed at reduced pressure to give a yellow oil. The yellow oil was poured over ice, basified with ammonium hydroxide, and extracted with methylene chloride. The methylene chloride solution was washed with water, dried with anhydrous sodium sulfate, and concentrated at reduced pressure to give a pale yellow solid. Recrystallization from a mixture of ether and methylene chloride gave cream colored prisms, mp 208°–210°.

EXAMPLE 24

8-Chloro-6-(2-chlorophenyl)-2H,4H-pyrazolo[3,4-d][2]benzazepine

The preparation of 8-chloro-6-(2-chlorophenyl)-2H,4H-pyrazolo[3,4-d][2]benzazepine was conducted in the same manner as the preparation of 8-chloro-6-(2-fluorophenyl)-2H,4H-pyrazolo[3,4-d][2]benzazepine to give the end product as a methylene chloride solvate as cream colored prisms, mp 142°–144° (foams).

EXAMPLE 25

3-[2-(2-Fluorobenzoyl)-4-chlorophenyl]-2-propenenitrile

A solution of 5.0 g (14 mmol) of 5-chloro-2'-fluoro-2-iodobenzophenone, 2 mL (14.3 mmol) of triethylamine, 2 mL (30 mmol) of acrylonitrile and 35 mg (1.5 mmol) of palladium acetate was refluxed under an atomsphere of argon for 16 hr. The mixture was diluted with 100 ml of 1N hydrochloric acid and the resulting precipitate was collected by filtration. The precipitate was washed with ether and air dried to give an off-white solid, mp 130°–133°.

EXAMPLE 26

(2-Chloro-5-nitrophenyl)(2-chlorophenyl)methanone

To 180 ml of concentrated sulfuric acid cooled to 0° in an ice bath was added 28 g (0.4 mol) of sodium nitrite in portions at such a rate that the temperature did not go above 10°. This mixture was warmed on a steam bath until a solution formed. It was then cooled to 30° and a solution of 110.68 g (0.4 mol) of 2-amino-5-nitro-2'-chlorobenzophenone in 300 mL of hot acetic acid was added at such a rate that the temperature did not exceed 40°. This mixture was stirred without heating for 2.5 hr, and then poured slowly into a mixture of 800 mL of concentrated hydrochloric acid and 80 g of cuprous chloride. This mixture was heated to 80° on a steam bath for 40 min until the foaming had subsided, poured into 2 l of water, and allowed to stand overnight. The solid was collected, washed with water and recrystallized from methanol to give product, mp 76°–79°.

An analytical sample prepared by recrystallization from methanol had mp 78.5°–80°.

EXAMPLE 27

(2-Chlorophenyl)(2-fluoro-5-nitrophenyl)methanone

A mixture of 900 mL of dimethyl formamide, 165 mL of toluene, 65.6 g (1.13 mol) of anhydrous potassium fluoride, and 74.6 g (0.252 mol) of (2-chloro-5-nitrophenyl)(2-chlorophenyl)methanone was stirred and heated to reflux. It was dried by distilling out 170 mL of distillate, and then heated under reflux overnight. It was cooled in an ice bath and diluted with 1 l of water and 100 mL of hexane. After 1 hr the gold-colored precipitate was collected and dissolved in 300 mL of methylene chloride. The solution, after separation of water, was dried over sodium sulfate and concentrated in vacuo. The residue was slurried in ether (cold) to leave crude 2-nitroxanthene-9-one. The ether solution was concentrated in vacuo and the residue recrystallized from methanol to give the product, 60°–64°.

An analytical sample prepared by recrystallization from methanol had mp 60°–64°.

EXAMPLE 28

3-(2-Chlorobenzoyl-4-nitrophenyl)-2,4-pentanedione

To a mixture of 100 mL of dimethyl sulfoxide, and 8 mL (78 mmol) of acetylacetone cooled in a cold water bath was added 8.8 g of potassium t-butoxide. There was an exotherm that was moderated by the addition of ice to the bath. After 0.5 hr, 11.2 g (40 mmol) of (2-chlorophenyl)(2-fluoro-5-nitrophenyl)methanone was added, and the reaction mixture was stirred 1 hr at room temperature. It was poured into a stirred mixture of 200 mL of ice water, 40 mL of 3N hydrochloric acid and a little ether. After 1 hr the solid was collected, washed with water and with hexane, and recrystallized from methanol to give the end product.

An analytical sample prepared by recrystallization from methanol had mp 138°-140°.

EXAMPLE 29

[5-Nitro-2-(3,5-dimethyl-1H-pyrazol-4-yl)phenyl]-2-chlorophenyl-methanone

A solution of 9 g (25 mmol) of 3-(2-chlorobenzoyl-4-nitrophenyl)-2,4-pentanedione in 60 mL of 0.5M hydrazine hydrochloride solution in aqueous ethanol was heated under reflux overnight and then concentrated in vacuo. The residue was partitioned between 100 mL of methylene chloride and 50 mL of water adjusted to pH 5 with concentrated ammonia. The organic phase was separated, washed with 50 mL of water, dried over sodium sulfate and concentrated in vacuo. The residue was crystallized from ether/hexane and recrystallized from ethyl acetate/hexane to give the end product.

An analytical sample prepared by recrystallization from ethyl acetate had mp 160°-162°.

EXAMPLE 30

(2-Chlorophenyl)[5-nitro-2-(1,3,5-trimethyl-1H-pyrazolyl)]methanone

To a mixture of 3.2 ml of methylhydrazine and 80 mL of ethanol was added 7.4 mL of concentrated hydrochloric acid and 14.4 g (40 mmol) of 3-(2-chlorobenzoyl-4-nitrophenyl)-2,4-pentane-dione. The mixture was stirred and heated under reflux for 6 hr. It was concentrated in vacuo and the residue was partitioned between methylene chloride and water adjusted to pH 6 with sodium bicarbonate. The organic phase was separated, dried over sodium sulfate and concentrated in vacuo. The residue was chromatographed over silica gel eluting with methylene chloride and 2% methanol in methylene chloride. The combined fractions of product were crystallized from ethyl acetate to give the end product, mp 146°-150°.

An analytical sample prepared by recrystallization from ethyl acetate/hexane had mp 146°-149°.

EXAMPLE 31

[5-Nitro-2-[3-(chloromethyl)-5-methyl-1H-pyrazol-4-yl]phenyl]-2-chlorophenylmethanone To a solution of 6.2 g (57.1 mmol) of t-butyl hypochlorite in 250 mL of methylene chloride was added 18.39 g (51.7 mmol) of the end product of Example 32, and the reaction mixture was allowed to stand at room temperature for 6 hr. It was then concentrated in vacuo and the residue crystallized from ether to give crude product.

An analytical sample prepared by recrystallization from aqueous methanol had mp 147°-149°.

EXAMPLE 32

(2-Chlorophenyl)[5-nitro-2-[3-(chloromethyl)-1,5-dimethyl-1H-pyrazol-4-yl]phenyl]methanone To a solution of 3 g (27.6 mmol) of t-butyl hypochlorite in 100 mL of methylene chloride was added 9.25 g (25 mmol) of the end product of Example 30. The reaction mixture got hot and the solvent boiled. It was stirred overnight and then concentrated in vacuo. The residue was collected with ether to give crude product, mp 142°-145°.

An analytical sample prepared by recrystallization from ethyl acetate had mp 145°-147°.

EXAMPLE 33

6-(2-Chlorophenyl)-3-methyl-8-nitro-2H,4H-pyrazolo[3,4-d][2]benzazepine

To ca. 50 mL of liquid ammonia was added 3 g (7.7 mmol) of the end product of Example 34. The ammonia was allowed to evaporate for 1 hr and then 25 ml of tetrahydrofuran was added. This mixture was heated under reflux to drive off the excess ammonia for 0.5 hr and then concentrated in vacuo. The residue was crystallized from a mixture of water and ether to give crude product.

An analytical sample prepared by recrystallization from acetonitrile was obtained as yellow prisms, mp 237°-241° (dec.).

EXAMPLE 34

6-(2-Chlorophenyl)-1,2-dimethyl-8-nitro-2H,4H-pyrazolo[3,4-d][2]benzazepine z-2-butenedioic acid salt (1:1)

To a mixture of 25 mL of tetrahydrofuran, 25 mL of liquid ammonia and 1 g of sodium iodide was added 5 g (12.4 mmol) of the end product of Example 32. This reaction mixture was stirred overnight while the ammonia evaporated. It was diluted with 100 mL of methylene chloride, washed with 50 mL of water, dried over sodium sulfate and concentrated in vacuo to leave a yellow tar. A solution of this tar and 1 mL of acetic acid in 100 mL of toluene was heated under reflux under a Dean-Stark water separator for 3 hr and concentrated in vacuo to a yellow oil. This was chromatographed on silica gel using methanol/methylene chloride (0.5%-5%) to elute. The fractions containing product were combined and treated with 1.35 g of maleic acid in ether to form the maleate. The solid was collected and washed with ether to give the maleate, mp 138°-142°.

An analytical sample prepared by recrystallization from 2-propanol had mp 135°-137°.

In a similar reaction starting with 17.1 g (42.3 mmol) of the end product of Example 32 there was obtained form the chromatography an oil which was crystallized from ether to give the end product, mp 140°-145°.

An analytical sample prepared by recrystallization from ethyl acetate/hexane had mp 141°-143°.

EXAMPLE 35

| TABLE FORMULATION (Wet granulation) | | | | |
|---|---|---|---|---|
| Item | Ingredients | mg/tablet | mg/tablet | mg/tablet | mg/tablet |
| 1. | 8-chloro-6-(2-fluorophenyl)-2H,4H—pyrazolo[3,4-d][2]benzazepine 6-(2-chlorophenyl)-3- | 1 | 5 | 10 | 25 |

| | TABLET FORMULATION (Wet granulation) | | | | |
|---|---|---|---|---|---|
| Item | Ingredients | mg/tablet | mg/tablet | mg/tablet | mg/tablet |
| | methyl-8-nitro-2H,4H—pyrazolo[3,4-d][2]benzazepine | | | | |
| 2. | Lactose | 202 | 232 | 261 | 280 |
| 3. | Modified Starch | 25 | 35 | 45 | 55 |
| 4. | Pregelatinized Starch | 20 | 25 | 30 | 35 |
| 5. | Distilled water q.s. | — | — | — | — |
| 6. | Magnesium Stearate | 2 | 3 | 4 | 5 |
| | Weight of tablet | 250 mg | 300 mg | 350 mg | 400 mg |

Procedure:
1. Mix Items 1-4 in a suitable mixer.
2. Granulate with sufficient distilled water to proper consistency. Mill.
3. Dry in a suitable oven.
4. Mill and mix with magnesium stearate for 3 minutes.
5. Compress on a suitable press equipped with appropriate punches.

EXAMPLE 36

| | TABLET FORMULATION (Direct compression) | | | | |
|---|---|---|---|---|---|
| Item | Ingredients | mg/tablet | mg/tablet | mg/tablet | mg/tablet |
| 1. | 8-chloro-6-(2-fluorophenyl)-2H,4H—pyrazolo[3,4-d][2]benzazepine 6-(2-chlorophenyl)-3-methyl-8-nitro-2H,4H—pyrazolo[3,4-d][2]benzazepine | 1 | 5 | 10 | 25 |
| 2. | Lactose | 221 | 217 | 212 | 181 |
| 3. | Avicel | 45 | 45 | 45 | 55 |
| 4. | Direct Compression Starch | 30 | 30 | 30 | 35 |
| 5. | Magnesium stearate | 3 | 3 | 3 | 4 |
| | Weight of tablet | 300 mg | 300 mg | 300 mg | 300 mg |

Procedure:
1. Mix Item 1 with an equal amount of lactose. Mix well.
2. Mix with Items 3 and 4, and the remaining amount of Item 2. Mix well.
3. Add magnesium stearate and mix for 3 minutes.
4. Compress on a suitable press equipped with appropriate punches.

EXAMPLE 37

| | CAPSULE FORMULATION | | | | |
|---|---|---|---|---|---|
| Item | Ingredients | mg/tablet | mg/tablet | mg/tablet | mg/tablet |
| 1. | 8-chloro-6-(2-fluorophenyl)-2H,4H—pyrazolo[3,4-d][2]benzazepine 6-(2-chlorophenyl)-3-methyl-8-nitro-2H,4H—pyrazolo[3,4-d][2]benzazepine | 1 | 5 | 10 | 25 |
| 2. | Lactose | 203 | 293.5 | 328 | 372.5 |
| 3. | Starch | 30 | 35 | 40 | 30 |
| 4. | Talc | 15 | 15 | 20 | 20 |
| 5. | Aerosol OT | 1 | 1.5 | 2 | 2.5 |
| | Capsule fill weight | 250 mg | 350 mg | 400 mg | 450 mg |

Procedure:
1. Mill Items 1, 2, 3 and 5 in a suitable mixer. Mill.
2. Add talc and mix well.
3. Encapsulate on suitable equipment.

What is claimed:
1. A compound of the formula

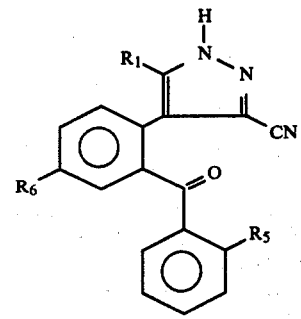

wherein $R_1$ is hydrogen or lower alkyl; $R_6$ is halo and $R_5$ is hydrogen or halo.

2. A compound of the formula

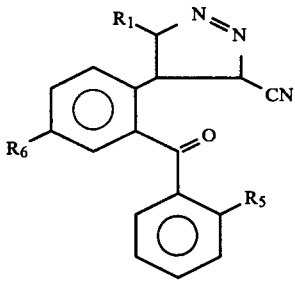

wherein $R_1$ is hydrogen or lower alkyl; $R_6$ is halo and $R_5$ is hydrogen or halo.

3. A compound of the formula

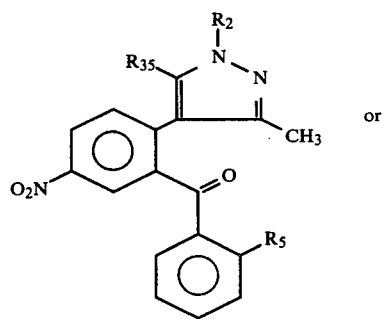

or

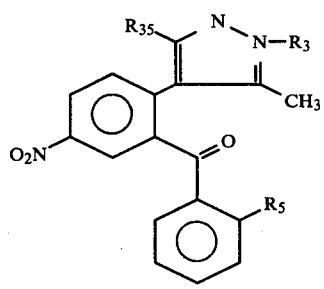

wherein $R_2$ and $R_3$ are selected from the group consisting of hydrogen, lower alkyl, $C_2$ to $C_7$ carboxylic acids, hydroxy $C_2$ to $C_7$ alkyl, $C_2$ to $C_7$ carboxylic acid esters and amides and the group $COR_{11}$ wherein $R_{11}$ is selected from the group consisting of alkoxy, amino or mono-lower alkyl amino; $R_{35}$ is hydrogen or lower alkyl and $R_5$ is hydrogen or halo.

4. A compound of the formula

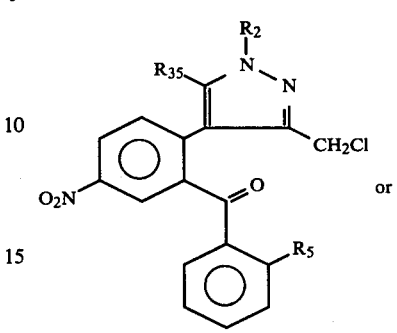

or

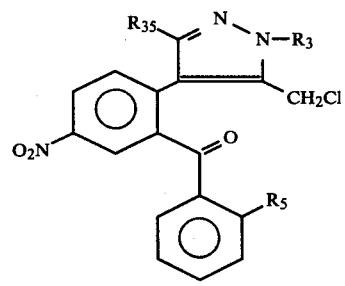

wherein $R_{35}$ is hydrogen or lower alkyl; $R_2$ and $R_3$ are selected from the group consisting of hydrogen, lower alkyl, $C_2$ to $C_7$ carboxylic acids, hydroxy $C_2$ to $C_7$ alkyl, $C_2$ to $C_7$ carboxylic acid esters and amides, the group $COR_{11}$ wherein $R_{11}$ is selected from the group consisting of alkoxy, amino, or mono-lower alkyl amino and $R_5$ is hydrogen or halogen.

5. The compound of claim 1 wherein $R_1$ is hydrogen and $R_5$ is halo.

6. The compound of claim 2 wherein $R_1$ is hydrogen and $R_5$ is halo.

7. The compound of claim 3 wherein $R_{35}$ is hydrogen and $R_5$ is halo.

8. The compound of claim 7 wherein $R_2$ and $R_3$ are hydrogen or lower alkyl.

* * * * *